United States Patent [19]

Shoesmith

[11] Plant 4,752

[45] Jul. 21, 1981

[54] CHRYSANTHEMUM NAMED COUGAR

[75] Inventor: Leonard H. Shoesmith, Woking, England

[73] Assignee: Pan-American Plant Company, West Chicago, Ill.

[21] Appl. No.: 170,075

[22] Filed: Jul. 18, 1980

[51] Int. Cl.[3] ..... A01H 5/00
[52] U.S. Cl. ..... Plt./76
[58] Field of Search ..... Plt./76

*Primary Examiner*—Robert E. Bagwill

*Attorney, Agent, or Firm*—Chas. W. Rummler

[57] ABSTRACT

A new chrysanthemum variety having a profuse production of unique and pleasing bronze flowers of medium size, borne on rigid stems above an abundant growth of dark green foliage. This plant is suitable for fall garden culture, with a medium response, as well as for year-round four inch pot production with a late eight week response. Its vigorous growth forms a mound of color providing a pleasing and attractive display when blooming in the fall garden.

4 Drawing Figures

BACKGROUND OF THE NEW PLANT

This new plant originated as a seedling of unknown parentage growing in a field of greenhouse chrysanthemum plants maintained at West Chicago, Ill., for breeding purposes and was discovered by me in 1976 in the course of my study and breeding efforts carried on with the object of producing new and superior garden chrysanthemums. Because of the unique bronze coloration of the flowers of this new plant, I reproduced the plant by means of cuttings at West Chicago, Ill., to test its habits and continued propagation, by cuttings and for successive generations, has demonstrated that the novel characteristics of this plant hold true from generation to generation and appear to be firmly fixed. At present, propagation of this new variety by cuttings is being carried on at Cortez, Fla., and at West Chicago, Ill.

DESCRIPTION OF THE DRAWINGS

This new chrysanthemum variety is illustrated by the accompanying drawings, of which sheet one is a full color photographic rendition showing a garden plant in full bloom; sheet two is a photographic close-up face view of flowers of the new plant which has been hand-painted to show the true colors of the flowers according to specification; and sheet three is a machine copy of typical leaves of this new variety.

DESCRIPTION OF THE NEW PLANT

The following is a detailed description of my new chrysanthemum variety based upon observations made in the fall of 1979 of plants grown at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—*Chrysanthemum morifolium.*
- *Commercial.*—Garden Chrysanthemum.

Form: Herbaceous bush of mound shape.
Height: The height varies according to plant culture.

Growth: Vigorous, upright and strong with a rapid growth rate.
Branching character: Caespitose.
Foliage:
- *Quantity.*—Abundant with many leaves.
- *Leaf size.*—Length — about 25 to 100 mm. Width — about 20 to 70 mm.
- *Leaf shape.*—Ovate with cleft margin.
- *Texture.*—Leathery.
- *Color.*—Upper side — 147A. Under side — 147C.
- *Venation.*—Pinnate.

THE BUD

Form: Globular.
Size: The size varies in both diameter and length.
Opening rate: Normal.
Color of florets:
- *When phyllaries first divide.*—167C.
- *When petals begin to unfurl.*—167B.

Phyllaries:
- *Number.*—Approximately 14.
- *Shape.*—Lanceolate.
- *Color.*—148B.

Peduncle:
- *Character.*—Erect and rigid and of various lengths.
- *Surface aspect.*—Canescent.
- *Color.*—148D.

THE FLOWER

Blooming habit: Intermittent, blooming once and profusely in the mid-season of fall.
Blooms:
- *Size.*—Medium. Diameter — about 50 to 70 mm.Depth — about 10 to 20 mm.
- *Borne.*—Cyme.

Shape:
- *When bloom first opens.*—Cup-shaped.
- *As the bloom matures.*—Flat.

Petalage:
- *Phyllaries.*—Approximately 14 in number.
- *Florets.*—Many ray florets and few disc florets.
- *Arrangement.*—Imbricated.
- *Form.*—Elliptic with entire margins and acuminate to acute apex.

Texture: Soft.
Appearance: Satiny.

Color:

*Outer petals.*—Body — 167A. Base — 167B. Reverse side — 163B.

*Inside petals.*—Body and base — 163C. Reverse Side — 163C.

Persistence: The flowers hang on and dry.

Peduncle: Strong, upright and of various lengths.

*Color.*—148D.

Fragrance: Typical chrysanthemum.

Lasting quality:

*On the plant.*—Three weeks. The flowers of this plant are not recommended for cut flower use.

REPRODUCTIVE ORGANS

Stamens:

*Arrangement.*—Syngenesious.

*Number.*—Few.

*Anthers.*—Size — insignificant. Color — yellow.

*Filaments.*—Length — insignificant. Color — insignificant.

*Pollen.*—Color — yellow.

Pistils: Number — one for each floret.

*Styles.*—Length — insignificant. Color — yellow.

*Stigmas.*—Color — yellow.

Ovaries: Inferior and bicarpellate.

This chrysanthemum plant is a new and unique variety particularly adapted for the fall garden and having a medium response. Its profuse production of bronze flowers are borne on rigid stems above an abundance of dark green foliage and the vigorous growth habit of this plant forms a mound of color in the fall providing spectacular garden decoration. This new chrysanthemum variety is also suitable for year-round four inch pot production under photoperiod culture with a late eight week response. The pot plants when in bloom produce an abundance of flowers which form a very pleasing mound shape display.

I claim:

1. A new variety of chrysanthemum plant for the fall garden, substantially as herein shown and described, particularly characterized by its profuse production of medium sized flowers having a unique bronze coloration and which form a mound shaped display; by its vigorous growth and caespitose habits; and by its adaptability to year-round pot production under photoperiod culture.

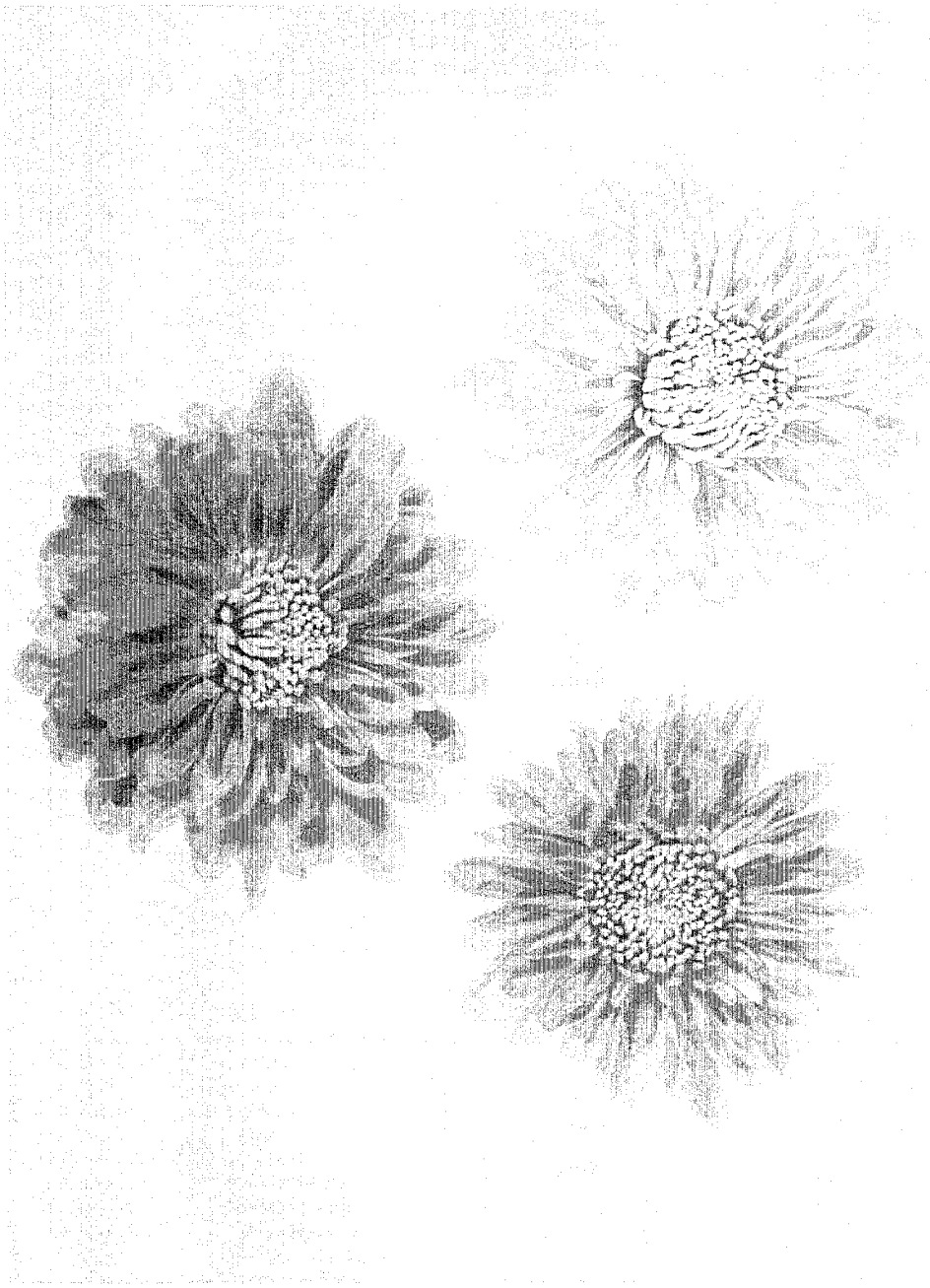

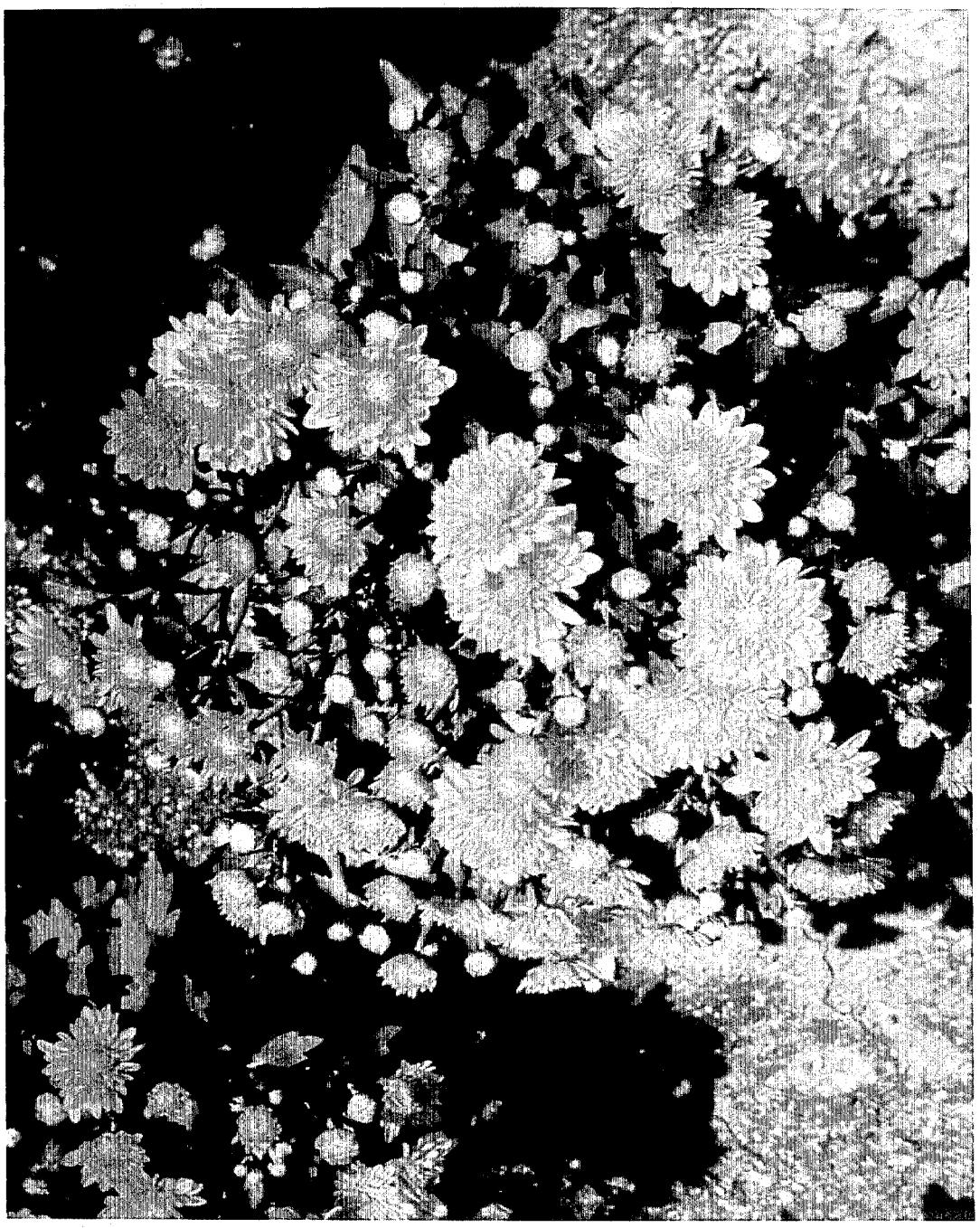

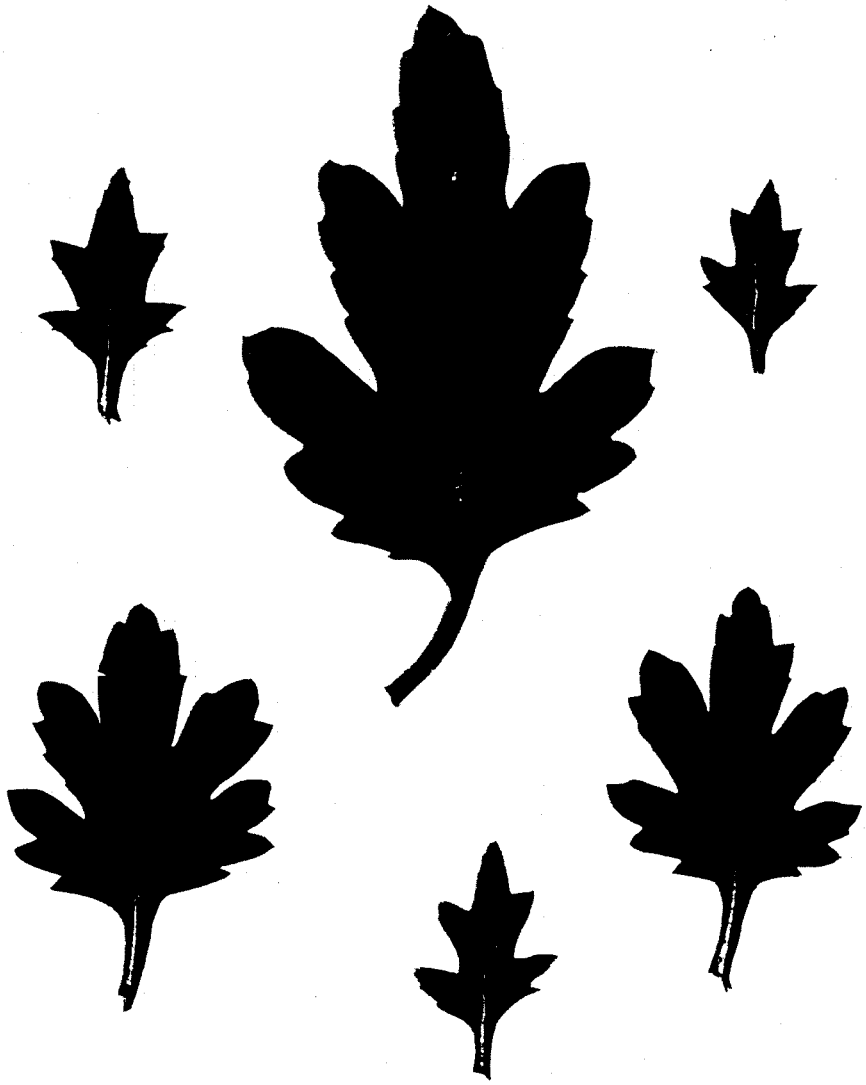

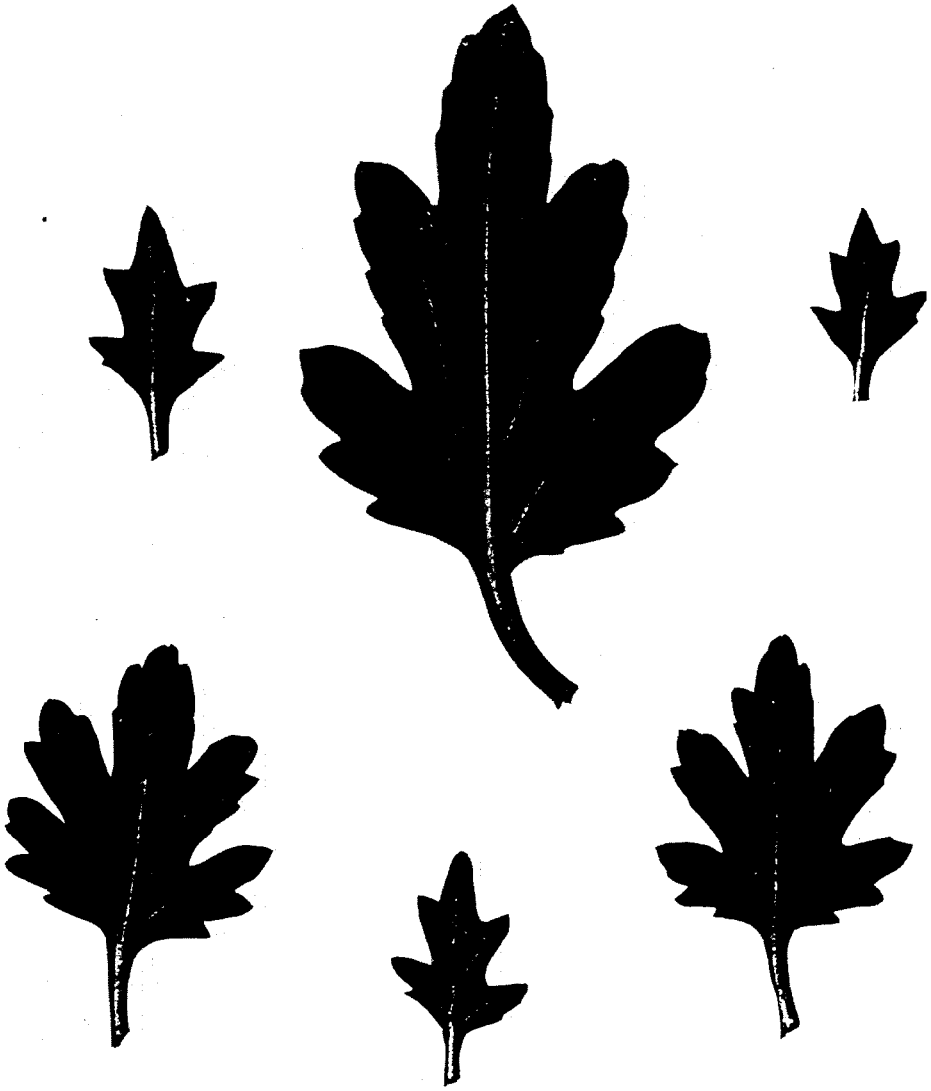

* * * * *